US006328709B1

United States Patent
Hung et al.

(10) Patent No.: US 6,328,709 B1
(45) Date of Patent: Dec. 11, 2001

(54) DEVICES AND METHODS TO IDENTIFY DUCTAL ORIFICES DURING NIPPLE ASPIRATION

(75) Inventors: David Hung, Belmont; Susan M. Love, Pacific Palisades; Julian Nikolchev, Portola Valley; William R. George, Santz Cruz, all of CA (US)

(73) Assignee: Pro Duct Health, Inc., Menlo Park, CA (US)

( * ) Notice: Subject to any disclaimer, the term of this patent is extended or adjusted under 35 U.S.C. 154(b) by 0 days.

(21) Appl. No.: 09/438,219

(22) Filed: Nov. 12, 1999

Related U.S. Application Data (60) Provisional application No. 60/108,449, filed on Nov. 13, 1998, and provisional application No. 60/127,507, filed on Apr. 2, 1999.

(51) Int. Cl.⁷ .................................................. A61M 1/06
(52) U.S. Cl. .............................................. 604/74; 604/514
(58) Field of Search ................................ 604/35, 73–77, 604/79, 118, 119, 140, 116, 500, 514

(56) References Cited

U.S. PATENT DOCUMENTS

| | | |
|---|---|---|
| 3,608,540 | 9/1971 | Sartorius . |
| 3,786,801 | 1/1974 | Sartorius . |
| 4,673,388 | 6/1987 | Schlensog et al. . |
| 4,680,028 | * 7/1987 | Stuart . |
| 4,709,657 | * 12/1987 | Gothard . |
| 4,740,196 | 4/1988 | Powell . |
| 4,767,417 | * 8/1988 | Boehringer et al. . |
| 4,772,262 | 9/1988 | Grant et al. . |
| 5,007,899 | 4/1991 | Larsson . |
| 5,042,978 | 8/1991 | Quenin et al. . |
| 5,471,994 | 12/1995 | Guirguis . |
| 5,476,490 | 12/1995 | Silver . |
| 5,762,640 | 6/1998 | Kajiwara et al. . |
| 5,798,266 | 8/1998 | Quay et al. . |

FOREIGN PATENT DOCUMENTS

WO 00/47247    8/2000  (WO) .

OTHER PUBLICATIONS

"Anatomy and Physiology of the normal and lactating breast" in *The Breast*, Bland ed. *Comprehensive Management of Benign and Malignant Diseases* 2nd ed vol. 2. 1998, ISBN 0–7216–6656–6.

Cobo. "Characteristics of the spontaneous milk ejecting activity occuring during human lactation." J. Perinnat. Med. 21 (1993).

"Breast Fluid cells help in early cancer detection" JAMA May 7, 1973; vol. 224, No. 6 pp. 823–827.

Leif et al. "TI centrifugal cytology of nipple aspirate." SO Acta Cytologica 24(3):255–261, 1980 May–Jun., [abstract only].

Love. "Collection and analysis of nipple aspirate fluid in the early detection of breast cancer." Windy Hill Technology, Inc. NAF Focus Group Study Sep. 18, 1998.

(List continued on next page.)

*Primary Examiner*—Anhtuan T. Nguyen
(74) *Attorney, Agent, or Firm*—Banner & Witcoff, Ltd.

(57) ABSTRACT

Devices, methods and kits for identifying a breast milk duct orifice capable of yielding fluid or releasing a keratin plug under a vacuum are described and claimed. The devices include a magnification lens integral to a nipple aspiration device or a nipple aspiration device having an attachment element for attaching a magnification tool to aid the practitioner to better observe a nipple surface under a vacuum. The devices also can include one or more access ports for such purposes as accessing the duct, marking the duct, or collecting fluid from the duct. The methods of nipple aspiration comprise identifying a duct that yields fluid or releases a keratin plug under a vacuum. The kits can comprise a device of the invention, a container for the kit contents, and instructions.

18 Claims, 7 Drawing Sheets

OTHER PUBLICATIONS

Petrakis. "Studies on the epidemiology and natural history of benign breast disease and breast cancer using nipple aspirate fluid." Distiguished Achievement award lectures, vol. 23 Feb. 10, 1993.

Rose. "Hormones and Growth factors in Nipple aspirates from normal women and benign breast disease patients." Cancer Detection and Prevention vol. 16, Issue 1 1992.

Ross et al. "Mammary Glands" in *Histology: a text and atlas* p. 711, ISBN 0–683–07369–9–.

Sartorius, "Cytologic evaluation of breast fluid in the detection of breast disease" J Nat'l Cancer Inst vol. 59 No. 4 Oct. 1977 pp. 1073–1080.

Sauter et al, "Nipple aspirate fluid: a promising non–invasive method to identify cellular markers of breast cancer risk" 1997 British J. Cancer 76(4):494–501.

Wrensch, et al. "Factors associated with obtaining nipple aspirate fluid:analysis of 1428 women and literature review" Breast Cancer Research and Treatment 15:39–51, 1990.

* cited by examiner

DEVICES AND METHODS TO IDENTIFY DUCTAL ORIFICES DURING NIPPLE ASPIRATION

CROSS-REFERENCES TO RELATED APPLICATIONS

The present application claims the benefit of provisional application No. 60/108,449, filed on Nov. 13, 1998, and of provisional application No. 60/127,507, filed on Apr. 2, 1999, under 37 CFR 1.78(3). The full disclosures of both applications are incorporated herein by reference.

FIELD OF THE INVENTION

The field of this invention is medical apparatus and methods for nipple fluid aspiration.

Classically, breast pumps have been made and used to aspirate mother's milk from lactating women in order to provide mothers the convenience of storing milk for their babies during times when mother and child could not be together. In non-lactating women, discharges and secretions of the nipple from the milk ducts have been obtained by removing the keratin material that plugs the ducts and using a nipple aspirator device to obtain small amounts of fluid secreted from the ductal orifices on the nipple surface. See page 51, Goodson W H & King E B, Chapter 4: Discharges and Secretions of the Nipple, The Breast: Comprehensive Management of Benign and Malignant Diseases (1998) 2nd Ed. vol. 2, Bland & Kirby Eds. W. B. Saunders Co, Philadelphia, Pa. pp. 51–74. This fluid is called nipple aspirate fluid or NAF. The human breast typically has from 6 to 12 ductal systems per breast that empty into the nipple through separate orifices, and in about 50–60% of non-lactating women fluid can be collected under vacuum pressure from at least one duct.

Cytological findings in NAF classified as moderate or atypical hyperplasia have shown a close association with histological findings of a similar classification. In correlating the NAF cytology findings with benign breast biopsies, 54% of those biopsies having histological lesions of atypical hyperplasia also had cytological findings of atypical hyperplasia. See King et al, (1983) J. Natl Cancer Inst 71: 115–1121. Also, women with moderate hyperplasia or atypical hyperplasia (as identified by random biopsy and subsequent histological examination of the biopsy specimen) have been shown to have a 1.5 to 5 times greater risk of breast cancer respectively than women with no biopsy. (See Goodson & King, (ref. 32) page 60). Histological lesions of moderate or atypical hyperplasia are associated with increase risk of breast cancer. See Petrakis et al, (1987) Lancet 2:505; Rogers and Page, (1979) Breast 5:2–7; Wellings et al, (1975) J. Natl Cancer Inst 55:231–273. It is currently also suggested that biomarkers identifiable in NAF may prove useful in breast cancer screening methods, or to evaluate response to a chemopreventative agent. See Sauter et al, British J. Cancer (1997) 76(4): 494–501. Therefore it may be of benefit to the medical and patient community to collect NAF for cytological or other analysis of breast conditions including breast cancer or its precursor conditions.

The present invention provides improvements to the existing NAF collection and aspiration devices to aid a practitioner to specifically identify a duct yielding fluid, and, if necessary or desired, the device provides a means to access the duct under the vacuum, mark the duct for further access or observation, or collect the fluid from a yielding duct before it mixes with other fluid in the collection cup.

Relevant Literature

Sartorius (1971) U.S. Pat. No. 3,608,540 describes a device for irrigating the breast ducts with saline solution under vacuum to be able to examine the retrieved solution for cytological abnormalities in the duct epithelial cells retrieved. Sartorius (1971) U.S. Pat. No. 3,786,801 describes a device for suctioning off breast duct fluid in a vacuum to be able to examine the epithelial cells in the duct fluid cytologically. Methods and kits for accomplishing nipple aspiration and collecting samples are claimed and described in U.S. Pat. No. 5,798,266 to Quay (1998).

Nipple aspiration techniques and device are described in Sartorius et al, "Cytologic evaluation of breast fluid in the detection of breast disease", Journal of the National Cancer Institute (1977) 59(4): 1073–80, Wrensch et al., "Breast cancer incidence in women with abnormal cytology in nipple aspirates of breast fluid", American Journal of Epidemiology (1992) 135(2): 130–41, and Sauter et al, "Nipple aspirate fluid: a promising non-invasive method to identify cellular markers of breast cancer risk", British Journal of Cancer (1997) 76(4):494–501.

A Company called Diagnostics, Inc. formed in 1968, produced devices to obtain breast ductal fluid for cytological evaluation. The devices included a nipple aspiration device to collect NAF from subjects. The devices were sold prior to May 28, 1976 for the purpose of collecting breast ductal fluid for cytological evaluation.

SUMMARY OF THE INVENTION

The invention provides devices, methods, and kits for aspirating and retrieving breast duct fluid. The device comprises an enclosure having an interior volume, an aperture adapted to circumscribe and seal against the base of a human breast nipple, and a vacuum port for connecting an external vacuum source to draw a vacuum in the interior volume. The device comprises a viewing window in the enclosure, optionally with a magnifying lens, where the window is positioned near the nipple surface so that a practitioner can look through the window and see an optionally magnified nipple surface under a vacuum. The magnification can provide the practitioner the ability to identify a ductal orifice, e.g. a ductal orifice from which fluid is secreted or from which a keratin plug is released under a vacuum. The device can further comprise one or more access ports for providing access to the nipple surface with a tool including, e.g. a ductal access tool, a ductal orifice marking tool, or a ductal fluid retrieval tool, wherein the access port also comprises a seal for maintaining vacuum before and during access with the tool. The ductal access tool can comprise a fiberoptic endoscope. The optional magnifying lens can be at an angle relative to the nipple surface, for example at an angle less than 90 degrees relative to the nipple surface.

The invention also provides a device for aspirating and retrieving breast duct fluid comprising an enclosure having an interior volume, an aperture adapted to circumscribe the base of a human breast nipple, and a vacuum port for drawing a vacuum with the interior volume, where the device comprises window, i.e. a transparent a solid surface that is clear and integral to the enclosure and that provides visual access to the nipple surface. The device further comprises at least anchor structure on the exterior of the enclosure to which a loupe, lens, microscope or other magnifying tool can be removably mounted so that a practitioner can see a magnified nipple surface under a vacuum. The device can further comprise one or more access ports for providing access to the nipple surface with a tool including, e.g. a ductal access tool, a ductal orifice marking tool, or a ductal fluid retrieval tool, wherein the access port also comprises a seal for maintaining vacuum before and during access with the tool.

The retrieval tool can comprise a lumen operably connected to a mechanism that provides suction in the lumen for drawing off fluid that collects on the nipple surface. The devices can comprise a skirt connected to the aperture made of a flexible material, wherein the flexible material is capable of maintaining a seal with the breast skin. The access port can be accessed with a fiberoptic endoscope.

The invention provides a method of identifying a breast milk duct having a ductal orifice (wherein the duct is capable of yielding fluid or releasing a keratin plug upon aspiration in a vacuum) comprising placing a device of the invention on the breast of a patient so that the nipple is covered, applying a vacuum to the device from the vacuum port, and identifying by magnification of the nipple surface at least one ductal orifice from which fluid is secreted or a keratin plug is released under a vacuum. The method can further comprise performing a task including marking a ductal orifice, accessing a ductal orifice or collecting fluid from a ductal orifice by placing a tool through the access port and accessing the nipple surface to perform the task. Marking can comprise marking the ductal orifice with a mark made by a reagent or tool including dye, ink, pen, plug, or wire. Accessing the duct can comprise accessing the duct with a tool comprising a lumen, a tool comprising a shaft without a lumen, or a fiberoptic endoscope. Collecting fluid from the duct can comprise collecting fluid with a tool including a lumen or an absorbent material. The vacuum port of the NAF device can comprise threading for screwing a compatibly threaded vacuum drawing device into the port.

The invention provides a kit comprising any of the devices above for aspirating and retrieving breast duct fluid for analysis, comprising also a container for the contents of the kit, and instructions for use of the device. The kit can further comprise a reagent or tool for marking the ductal orifice, a tool to access the duct, or a tool for collecting fluid from the duct.

Any of the NAF retrieval devices of the invention can be sterilized for single use, and thus the device is thereafter not sterile for use subsequent to the first use. In practicing the methods of using the NAF retrieval devices, the device can be sterilized for single use prior to placing the device on the nipple; and the device will thus thereafter not be sterile for use subsequent to the first use. Kits for aspirating and retrieving breast duct fluid for analysis can comprise a NAF retrieval device that is sterilized for single use so that the device is thereafter not sterile for use subsequent to the first use.

DESCRIPTION OF THE SPECIFIC EMBODIMENTS

The following preferred embodiments and examples are offered by way of illustration and not by way of limitation.

The presence or ability to yield fluid from a milk duct under the type of vacuum pressure applied to the breast and nipple with nipple aspiration is associated with increased risk of developing breast cancer. See Wrensch et al (1992) Am J. Epidemiol 135:130–141. Thus it would be advantageous to identify a ductal orifice of the duct yielding fluid upon nipple aspiration for further observation or analysis of that duct. However, generally during nipple aspiration the fluid is pooled in a collection receptacle or cup, and the ductal orifices are not identified. Also, generally during nipple aspiration, ductal orifices have not been accessible in the past. The present invention improves upon existing NAF devices by providing the practitioner a means to see more detail on the nipple surface than is seen when the nipple is enclosed in other NAF devices or breast pumps and to provide a practitioner a means to see more detail than is seen on the nipple surface with the naked eye. Thus the invention provides e.g. a means to detect the location on the nipple surface where fluid is secreted or from which a keratin plug is released under a vacuum and thus to identify a ductal orifice. Following such identification, the present invention provides at least one access port that makes it possible for the orifice to be accessed, marked, or to collect fluid at the orifice from the fluid-yielding duct before the fluid has a chance to mix with other fluid in the collection cup. The precision and ability to control this access is greatly enhanced by performing the access-related task under a vacuum guided with the aid of magnification.

Although breast pumps exist for pumping mother's milk, special adaptations have been made to devices to retrieve ductal fluid of non-lactating women, primarily in response to the challenge of getting fluid from the non-lactating breast. The present invention provides improvements to NAF collection devices to provide the practitioner the advantage of identifying the ductal orifice under a vacuum while the nipple surface is distended from the vacuum pressure. Under a vacuum some of the milk ducts of non-lactating women yield fluid and/or release a keratin plug, and where the vacuum pressure distends the nipple surface, some of the ductal orifices may appear visible to a practitioner viewing the distended nipple surface under magnification (i.e. distinguishable from other topography of the nipple surface such as crevasses and/or folds or pits in the nipple skin). With current NAF devices, fluid is aspirated and immediately pooled into the collection cup. Location and/or identification or marking of the ductal orifice is not made primarily due to the opaqueness of the cup material and/or lack of visual aid provided with the aspiration device. The fluid secretions from milk duct orifices can be minute, and thus detection of them are facilitated by magnification. In addition, NAF devices have lacked elements that aid a practitioner to access the nipple surface under a vacuum. The present invention overcomes these obstacles and difficulties by providing improvements in the form of additional features that can be added or adapted to most any NAF collection device.

The NAF device of the present invention comprises an enclosure with an interior volume. The enclosure having an interior volume may be an enclosure of any shape suitable for nipple aspiration and/or collection, or for another as yet undesignated purpose pertaining to the task of getting ductal fluid out of the nipple by applying vacuum pressure. Because generally, not much fluid is expected from non-lactating women, the interior volume may be designed to be small and to reside close to the nipple. Shapes for such enclosures can include cylinders, cones, inverted cones, and other shapes. Many breast fluid collection devices having enclosed interior volumes have been described in the art. See such NAF collection devices as are described in, e.g. Sartorius (1971) U.S. Pat. No. 3,786,801, Quay (1998) U.S. Pat. No. 5,798,266, Sartorius et al, Journal of the National Cancer Institute (1977) 59(4):1073–80, Wrensch et al., American Journal of Epidemiology (1992) 135(2):130–41, Sauter et al, British Journal of Cancer (1997) 76(4):494–501, and Leif et al (1980) SO Acta Cytologica 24(3):255–61.

Other devices for obtaining fluid and/or cytology monolayers from human tissue may be adaptable to the purpose of NAF collection and describe enclosures with an interior volume, such as those devices described in e.g. Mitchen (1989) U.S. Pat. No. 4,844,098, Guirguis (1995) U.S. Pat. No. 5,471,994, and Kajiwara et al (1998) U.S. Pat. No. 5,762,640.

Breast pumps for the purpose of aspirating milk from lactating women also have enclosures with an interior volume and may be adaptable to collect NAF, including those devices described in e.g. Adams (1982) U.S. Pat. No. 4,323,067, Bachman et al (1998) U.S. Pat. No. 5,843,029, Niederberger (1998) U.S. Pat. No. 5,810,772, Silver (1998) U.S. Pat. No. 5,797,875, Williams (1998) U.S. Pat. No. 5,749,850, Jelks (1997) U.S. Pat. No. 5,616,125, Palmer (1996) U.S. Pat. No. 5,571,084, Meyers et al (1996) U.S. Pat. No. 5,542,921, Samson (1995) U.S. Pat. No. 5,415,632, Aida et al (1994) U.S. Pat. No. 5,295,957, Larsson (1991) U.S. Pat. No. 5,049,126, Stuart (1987) U.S. Pat. No. 4,680,028, Yuan (1990) U.S. Pat. No. 4,892,517, Adams (1981) U.S. Pat. No. 4,263,912, Adams (1981) U.S. Pat. No. 4,249,481, Aida et al (1988) U.S. Pat. No. 4,759,747, Friedman (1985) U.S. Pat. No. 4,501,585, Larsson (1989) U.S. Pat. No. 4,794,915, Schlensog et al, (1987) U.S. Pat. No. 4,673,388, Powell (1988) U.S. Pat. No. 4,740,196, and the breast pumps described in Johnson, (1983) Clinical Pediatrics (January) p. 40–45.

In addition the NAF device can have such additional elements as a breast pump insert for stimulating fluid release from the ducts as described in U.S. Pat. No. 5,885,246 to Ford, a flexible breast receptor as described in U.S. Pat. No. 4,680,028 to Stuart, a device for monitoring the fluid yield as described in U.S. Pat. No. 5,827,191 to Rosenfeld, and a container using a mass of porous material for liquid retention as described in Quenin et al, U.S. Pat. No. 5,042,978.

Nipple aspirate fluid can be retrieved as described in e.g. Goodson W H & King E B, Chapter 4: Discharges and Secretions of the Nipple, The Breast: Comprehensive Management of Benign and Malignant Diseases (1998) 2nd Ed. vol 2, Bland & Kirby eds. W. B. Saunders Co, Philadelphia, Pa. pp. 51–74; Wrensch et al., (1992) American Journal of Epidemiology. 135(2):130–41; and Sauter et al (1997) British Journal of Cancer. 76(4):494–501. Cells of the lesion can be retrieved by collecting the ductal fluid that contains some of these cells, e.g. by aspirating the nipple to obtain nipple aspirate fluid, e.g. as described in Petrakis (1993) Cancer Epidem. Biomarker Prev. 2:3–10, Petrakis (1986) Breast Cancer Res. Treat 8: 7–19, Wrensch et al (1992) Am. J. Epidem. 135:130–141, Wrensch et al (1990) Breast Cancer Res Treat 15: 39–21, and Wrensch et al (1989) Cancer Res. 49: 2168–2174.

The device provides an aperture adapted to circumscribe the base of a human breast nipple. The aperture is designed to enclose at least the nipple, and possibly also the areola and/or part of the breast, depending on both the size of the device and the relative dimensions of the nipple, areola, and breast of the subject. The aperture thus can be any size suitable for enclosing the nipple, the nipple and a portion of the areola, the nipple and the areola, or the nipple, the areola and a portion of rest of the breast. The circumference of the aperture contacts the nipple, areola, or breast tissue to make a seal so that vacuum pressure can be created at the nipple surface. Thus the aperture may have, e.g. any of the suitable shapes or qualities of the NAF devices, fluid collection devices or mother's milk breast pumps listed above. The sides of the cup can have markings to help identify the height of the nipple (see e.g. FIG. 5).

Figure 5:
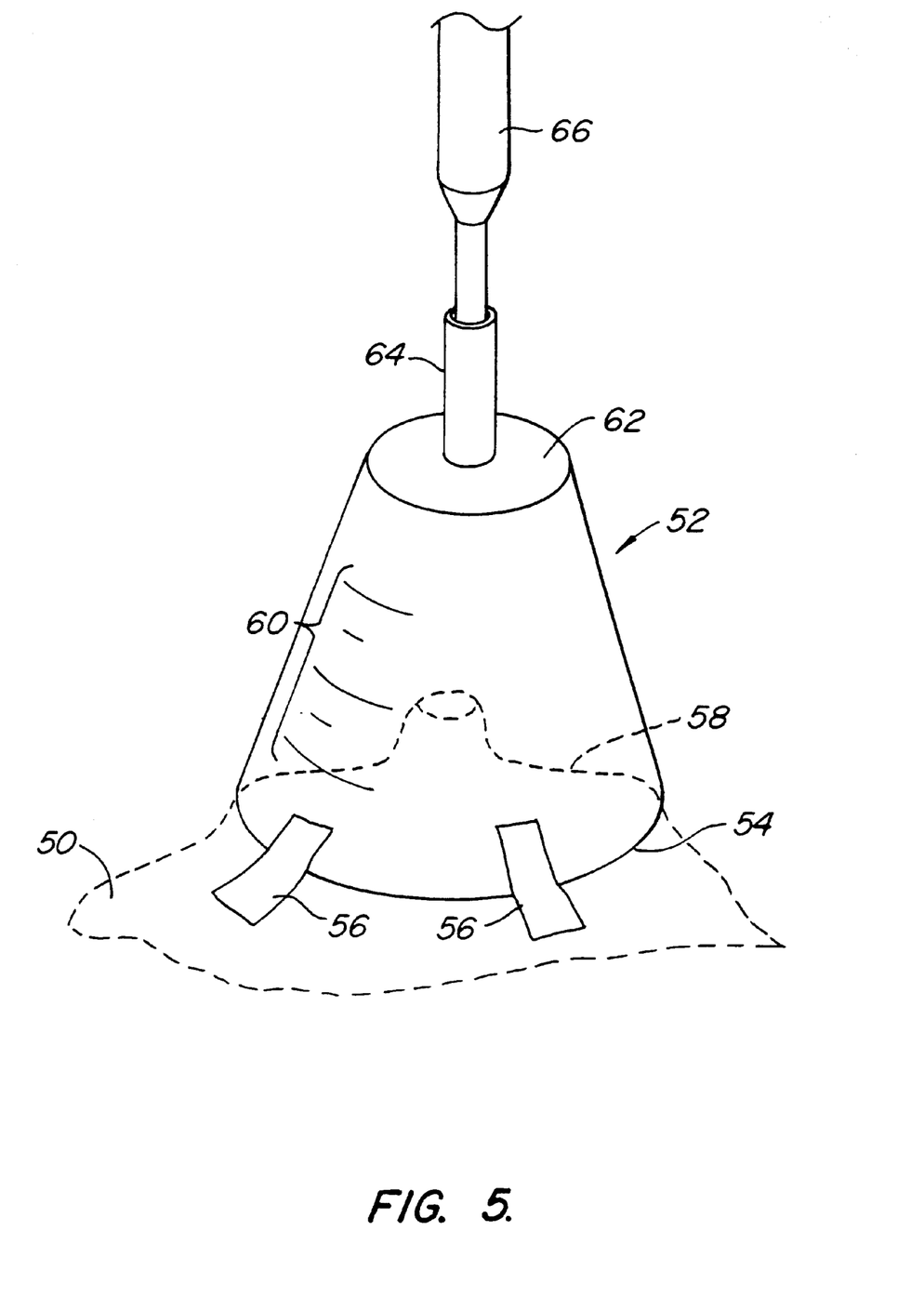
FIG. 5 shows a NAF cup having a base larger in diameter than the top, and a vacuum port at the top center.

The aperture can have a skirt connected to it. The skirt can be made of flexible material, e.g. a flexible polymer such as silicone used in medical devices. The skirt can be of varying length. Thus, the skirt can be extend from the aperture e.g. in a range of about 2 centimeters to about 10 centimeters or more. The skirt should be capable of resting on the breast tissue and maintaining a vacuum seal so that the vacuum in the enclosure is not interrupted. The skirt can help to absorb some of the pressure applied to the breast tissue during aspiration and thus can help to reduce any discomfort. Where the skirt is broad and covers much of the breast tissue, the skirt can provide protection to the breast tissue upon manipulation and/or squeezing of the breast. For larger skirts, petroleum jelly may be placed on an interior portion of the skirt to ensure a tight seal with the breast skin and so that the seal is not broken when the breast itself is squeezed in an effort to increase the NAF yield. Instead of a skirt, attachment tape or other fixative strip can be placed on the cup opening that contacts the breast skin, e.g. as depicted in FIG. 5.

The NAF device of the invention provides a vacuum port for drawing a vacuum at the nipple surface. The vacuum port may be located at the base of the cup or NAF receptacle, or on the sides of the receptacle. The port is used for pulling air out of the NAF chamber to provide vacuum pressure on the surface of the nipple. The port is of sufficient size and shape that a device capable of drawing air from the enclosure having the interior volume can fit into the port and create sufficient vacuum pressure over the nipple. The mechanism for creating the vacuum pressure can be e.g. a vacuum conduit available in a hospital or clinic or simply a syringe, that when drawn back (i.e. opened) creates negative pressure at the nipple surface. Ports suitable for this purpose are described in the literature and patents cited above.

The device can comprise a magnifying lens within the solid support material that forms the enclosure having the interior volume. For example, the magnifying lens can be at the base of an inverted cup that is placed on the nipple. Looking down on the nipple surface through the base of the inverted cup, a practitioner looks through the magnifying lens and sees a magnified nipple surface. The magnifying lens may be placed at an angle with respect to the nipple surface, e.g. in an ellipse or truncated ellipse in order to provide a practitioner better visual access to the nipple surface (see FIG. 4). The angle can be, for example an angle of less than 90 degrees relative to the nipple surface, or approximately in a range from about 30 degrees to about 50 degrees relative to the nipple surface.

Figures 6A, 6B:
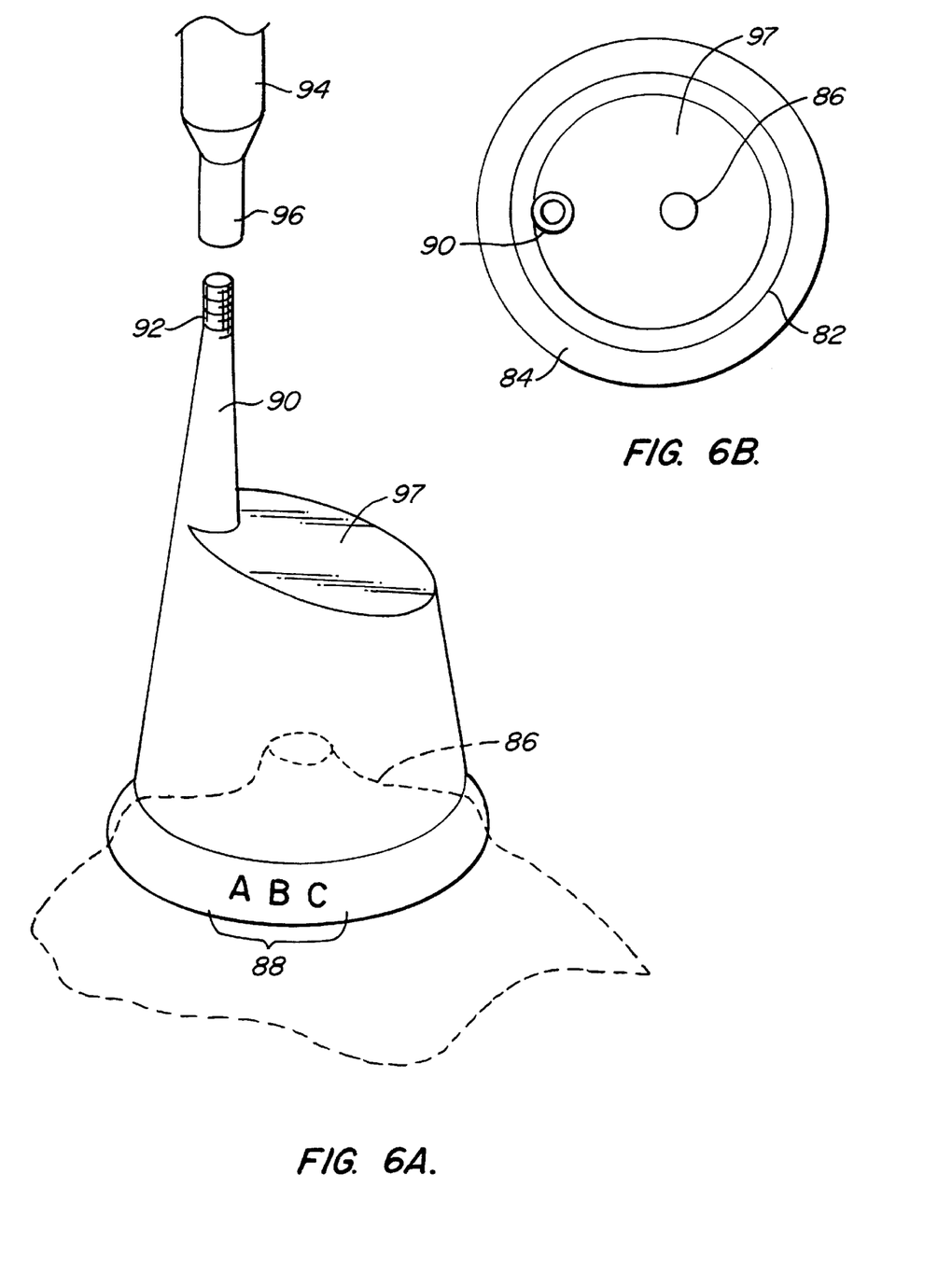
FIG. 6 shows a NAF cup having a slanted top with magnification and a vacuum port at the peak of the slant, the vacuum port having internal threads for screwing the syringe into to withdraw the air from the chamber. The NAF device also has labeling provided on the skirt to identify the device maker.

In general the magnifying lens is most appropriately placed in proximity to the nipple surface, where the practitioner can see all or mostly all of the nipple surface by looking through the lens. The lens is positioned so that the practitioner can identify and resolve the location of minute changes on the nipple surface. These changes can include, e.g. fluid accumulation on the nipple surface, loss of a keratin plug from a ductal orifice, and other features that appear on the nipple surface under a vacuum that would indicate the likely or actual location of a ductal orifice on the nipple surface, including e.g. changes in the nipple surface topography with the distention of the nipple surface caused by the vacuum. The placement of the magnification lens can be at the top of the cup, or on the sides of the cup or both. The top of the cup can be parallel to the nipple surface (see e.g. FIGS. 1, 2, 3, and 5) or may be at an angle relative to the nipple surface (see e.g. FIGS. 4 and 6).

The magnification strength of the lens is that degree of magnification that provides the practitioner a resolved and magnified view of the nipple surface. Preferably, the magnification provides the practitioner with additional visual details to aid in ductal orifice identification. For example, the resolution should be about the resolution necessary for seeing a small breast duct orifice and/or keratin plug at the nipple surface, and for aiding the practitioner to distinguish between a crevasse in the nipple surface and a ductal orifice. Primarily, however, the magnification should be of sufficient strength and resolution to provide the practitioner a visual ability to identify accumulation of minute moisture on the nipple surface at a discrete location. The magnification is also of sufficient strength and resolution to provide the practitioner a visual ability to identify a keratin plug at the nipple surface or the release of a keratin plug. The discrete location at which moisture accumulates or from which a keratin plug is released is assumed in most cases to be the site of a ductal orifice. The resolution needed for the device to work optimally may depend on such variables e.g. as the distance from the nipple surface that the lens is located, and the resolution capabilities of the practitioner. The lens can be made of glass and/or standard magnification materials. The lens is integral to the aspiration cup. The integral lens can be rigidly fixed in the cup (i.e. no easily removable) or the integral lens can be removable from the cup base (e.g. the lens can snap in and out) in order to insert lens pieces of greater or lesser strength of magnification. The removable lens is considered integral to the device because when snapped into place at the cup base it allows creation of and/or maintains the vacuum seal in the enclosure. The ability of the magnifying lens to snap in and out of the base of a NAF collection cup can provide the opportunity for using a disposable NAF cup into which a reusable and sterilized magnifying lens can be snapped for each new procedure.

The device can comprise one or more access ports. An access port can be located at any spot on the cup or NAF receptacle that provides easy access to the nipple surface with a tool. An access port is probably most useful if located at the base of the inverted cup, and at the base off to one side of center so that the tool can access the nipple surface and the practitioner still has some viewing space of the nipple surface to watch and guide the tool by. An access port may be located on a side of the cup, receptacle or enclosure near the base, provided good access to the nipple surface is maintained from the position. The access port is sealed or provided with a seal, such as e.g. a passive valve made from a rubber ring or gasket that is closed when not accessed and which closes when and during access of the port by a tool. The seal provides that access to the access port does not interfere with the vacuum pressure inside the enclosure, and also provides that vacuum pressure within the enclosure can be maintained even while an access port is being used to access the nipple surface.

An access port is used for providing access with a tool to the nipple surface. The tool can access the access port for any purpose including e.g. the purposes of accessing a duct through the ductal orifice, marking the ductal orifice at the spot where moisture accumulates under vacuum pressure, or a spot that the practitioner believes is likely a ductal orifice for other reasons (e.g. release of a keratin plug), or for collecting the fluid secreted from a specific duct.

The tool for accessing the duct can be e.g. a lumen or shaft for penetrating the duct. The lumen can be, e.g. a catheter, a cannula, or a hollow needle or hollow probe. The shaft can be e.g. a wire, a needle, or a probe. The access tool may also be a fiberoptic endoscope capable of accessing a duct and probing inside the duct for visual or other information. The fiberoptic endoscope can be, e.g. the fiberoptic scope (a ductoscope) as described in Okazaki et al (1991) Jpn J Clin Oncol 21(3) 188–193.

The tool can mark the ductal orifice once it is identified by the accumulation of moisture on the nipple surface. Thus, e.g. the tool can be a pen capable of marking nipple skin. The marking substance can be visible to the naked eye, or may be a substance requiring special light (e.g. fluorescent light) to see. The light may be an integral element in the NAF device, or the light may be attachable at an attachment point, much like a lens or loupe can be attached and/or removable from the device provided the device is equipped with an attachment member for facilitating such attachment. The mark made on the nipple surface at a ductal orifice can be permanent or semi-permanent.

The tool can also be for collecting fluid from the ductal orifice as the fluid is secreted. Thus, e.g. the tool can be a lumen, e.g. a capillary tube into which the fluid is drawn by capillary action. The lumen may also be connected to a mechanism capable of providing suction in the lumen to draw the fluid from the nipple surface into the lumen, and from the lumen into a collection tube or other receptacle. The advantage of using a collection tool in an access port is that fluid collected at the ductal orifice will not mix with other fluid in the collection cup, and thus can be analyzed to determine the condition of the specific duct from which the fluid came. The suction mechanism at the lumen may be a syringe capable of drawing the fluid from the nipple surface into the lumen and/or syringe.

It is contemplated that the nipple aspiration device can have multiple access ports, e.g. where multiple ducts are to be accessed under a vacuum at the same time, or approximately the same time.

The device may have an enclosure with an interior volume, an aperture adapted to circumscribe the base of the human breast nipple, a vacuum port for drawing a vacuum within the interior volume, and can comprise a solid surface that is clear and integral to the enclosure and near to the nipple surface so that it provides visual access to the nipple surface. Such a device comprises also at least one point on the exterior of the device to which a loupe, lens, microscope or other magnifying tool can be affixed so that a practitioner can see a magnified nipple surface. The attachment element is capable of attaching a lens, loupe, microscope or other magnification tool to the NAF device so that a ductal orifice that yields fluid or releases a keratin plus, or which is in some way identifiable due to the aid of the magnification can be identified. The attachment is thus detachable which is advantageous with use of disposable or sterilizable NAF collection cup, for example.

Another advantage to this feature of an attachment element is that it provides the practitioner the ability to affix a lens, loupe, or microscope that has an appropriate magnification strength for the situation. The magnification angle can also be adjustable at the attachment. The element capable of attaching the lens, loupe, microscope or other magnification tool can be a bar, a snap, a pin to attach to a ring, or other attachment mechanism for attaching a means to accomplish magnifying the nipple surface for the practitioner. The enclosure or cup has at least one surface that is relatively clear through which the magnification can occur, for example a clear glass surface so that the magnification is not impeded by cloudy resolution through an opaque or slightly obscure solid surface. The attachment is designed so that the vacuum port and one or more access ports can be located conveniently in useful placement positions on the exterior surface of the enclosure.

The attachment element can be designed to accommodate the attachment of a microscope for achieving a visualization of a highly magnified nipple surface. The case of attachment of the microscope to the NAF device while the nipple is under vacuum leaves the practitioner with hands free to manipulate a tool in an access port and thus perhaps to identify, access, or mark the breast ducts, and/or to collection yielded fluid from a duct. The microscope can be connected to a video monitor to record or monitor the procedure.

As with the other embodiments, the vacuum port can be located on the side of the cup or at the top or base of the cup or enclosure. An access port can be located at the top or on the side, near the top or base of the inverted cup. Preferably the access port is located at the base or top of the cup so that the tool can extend down to the nipple surface and the practitioner can have maximum control of the tool. Both the vacuum port and one or more access ports can be located at the base of the cup, or where there are multiple access ports, some may be located on the sides of the enclosure, preferably up towards the base to give the best angle for access. The positioning of the access port is designed to optimize access to the nipple surface. An access port has a seal (e.g. a gasket, ring or other material placed in the port to form around the accessing tool) so that access with a tool, e.g. an access, marking or collecting tool does not interrupt the vacuum inside the enclosure. A seal is useful in the access port because optimal accessing, marking or collecting may occur with the distention of the nipple surface, as occurs when the surface is under vacuum pressure. The vacuum port may also have a seal, or some means of attaching tightly to the mechanism that draws the vacuum so that the vacuum pressure inside is maintained once it is established.

The device having the attachment element can comprise a cup or other receptacle having an aperture that has a skirt made of a flexible material (e.g. a polymeric material) designed to cover at least part of the breast. The flexible material is designed to make a seal with the breast skin so that a vacuum can be established and maintained at the nipple surface. The flexible material can provide protection to the breast tissue upon application of the cup and application of the vacuum. A skirt of a flexible material (e.g. flexible polymer material) surrounding the aperture of the cup provides some reduction in the discomfort if the cup is pushed into the nipple to get a good fit, and/or during the time when the nipple is being aspirated and drawn into the cup by the vacuum in the enclosure. Other elements and details of the skirt are described above for other embodiments. The skirt may have lettering or other markings on it to identify the maker of the NAF device, such as the name of the company or a logo or both.

The vacuum port of the NAF device can comprise threading for screwing a compatibly threaded vacuum drawing device into the port. The threading is placed inside the lumen of the vacuum port for receiving a compatible threads on the outside of the lumen of a vacuum drawing device, such as a syringe. The screwing provides a tight seal from air leakage either into or out from the chamber created by placing the NAF cup over the nipple.

In addition to the other features of the NAF retrieval device, it may possess the property of being capable of sterilization once. Thereafter, after the first use, the device may not be subsequently sterilized, so as to ensure that any subsequent sterilizations are not incomplete or inadequate thereby jeopardizing the safety of the NAF procedure. For example, the NAF device may have some or all components made of a plastic or other synthetic material that is sterilized during or after manufacture and is assembled into the device in a sterile field, but which will not withstand an autoclave procedure for re-sterilization, or which will chemically react with common solvents used in laboratory or office sterilizations conducted for the purpose of reuse of the device. The methods described below may incorporate such a limitation to repeat sterilization, and the kits also described below may contain devices which are sterilized for single use only.

The invention provides a method of identifying a breast milk duct having a ductal orifice where the duct is capable of yielding fluid or releasing a keratin plug upon aspiration in a vacuum. The steps of the method comprise placing the device described above (either the device with a fixed magnification lens in the cup or enclosure (e.g. the base of the cup) or the device having an attachment means for attaching a magnification lens, loupe, microscope or other magnification tool) on the breast of a patient, covering the nipple, and applying a vacuum to the device from the vacuum port and identifying by magnification of the nipple surface at least one ductal orifice from which fluid is secreted or a keratin plug is released or other identifiable change occurs on the nipple surface as it is place under vacuum pressure. For example, the distended nipple surface that occurs under vacuum pressure may be enough when coupled with the magnification aid of a lens or a loupe to allow the practitioner to identify ductal orifices, because when distended, some of the ducts on the nipple surface may be more identifiable (when aided by the magnification) than on a non-distended nipple surface.

Additionally the method can include performing a task by accessing an access port with a suitable tool. The task can be, e.g. marking the ductal orifice, accessing the ductal orifice or collecting fluid from the nipple surface at the ductal orifice, by placing a tool through the access port and accessing the nipple surface to perform the task.

Marking the ductal orifice can occur with a mark made by a reagent or tool including dye, ink, pen, plug, or wire. For example a pen capable of marking nipple skin and having a fine point can be put into the access port and used to mark the site where fluid begins to accumulate on the nipple surface.

Accessing the duct can comprise accessing the duct with a tool having a lumen, and a tool comprising a shaft without a lumen. Thus, the duct can be accessed by e.g. a cannula, catheter, or other lumen, or by a solid metal probe, or needle, for example a galactography dilator needle or probe. The access tool can be a fiberoptic endoscope used to access a duct and retrieve visual information from inside the duct.

Collecting fluid from the duct can comprise collecting fluid with a tool including, e.g. a capillary tube, or a catheter, including e.g. a lumen or catheter connected to a device that provides suction through the lumen to draw fluid from the nipple surface. Collection can also be made with a tool having at its tip an absorbent material, e.g. a small filter, gauze, or other absorbent material to soak up the secretions from a duct on contact.

Figure 1:
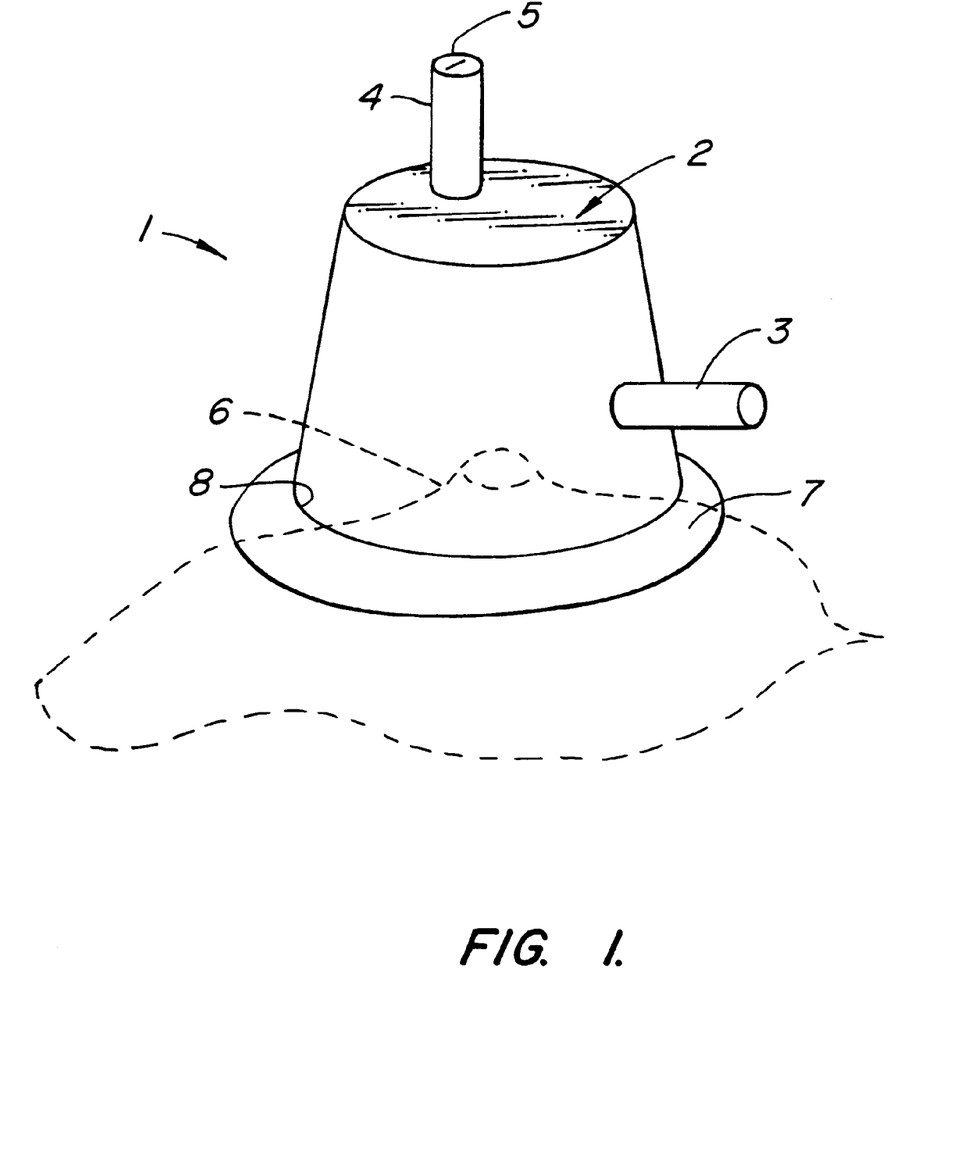
FIG. 1 shows a NAF collection device having a magnifying lens.

Turning now to the figures, FIG. 1 shows a NAF collection device having a collection cup 1 with a magnifying lens 2 at the base of the cup so that when the cup is inverted to cover the nipple 6 the magnifying lens provides the practitioner with a magnified view of the surface of the nipple. The cup aperture 8 is connected to a skirt 7 of flexible material. Vacuum port 3 provides a hole from which the air can be drawn out of the cup to create a vacuum at the nipple surface so that the fluid can be aspirated from the ducts. The vacuum port can be accessed with a syringe capable of drawing out air and creating the vacuum necessary for aspiration. Access port 4 can be on or near the top of the cup and provides the practitioner with a means to enter the vacuum chamber surrounding the nipple with a tool. The access port has an internal seal 5, such as a duck bill valve or other common pneumostatic seal, for maintaining suction when the port is accessed with a tool. During a NAF collection procedure, cup 1 is placed over nipple 6 and positioned so that magnifying lens 2 has a clear view of the nipple, and the nipple is centered under the magnifying lens 2 and inside the cup 1. The cup aperture 8 and skirt 7 are replaced if the nipple is off center, and a seal is made with the skirt 7 on the breast. A syringe or other vacuum generating tool is placed at the vacuum port 3 to draw air from the chamber created by placing the cup on the nipple. The syringe is emptied before placement in the port and air is drawn into the syringe from the chamber to a maximum designated volume marking on the syringe (e.g. in a range from about 2 cc to about 20 cc; most commonly in a range from about 5 cc to about 10 cc). Access port 4 can be closed, e.g. where pooled fluid can collect in the cup or be collected immediately after removing the NAF cup from the breast; or the access port can be accessed by a tool in order to collect the fluid as the fluid develops on the nipple surface. The tool can having a lumen to draw up the fluid, e.g. a capillary tube or a catheter.

Figure 2:
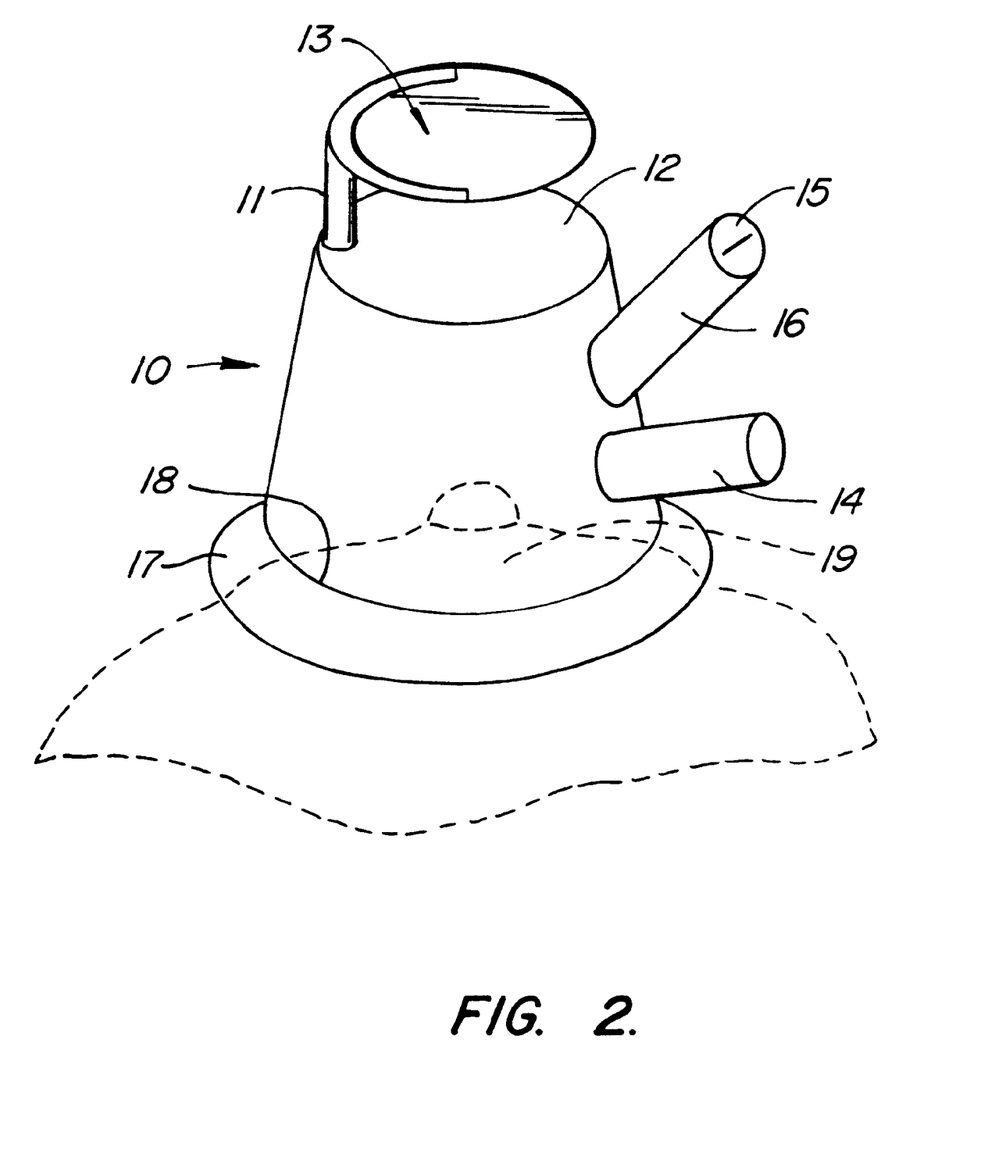
FIG. 2 shows a NAF collection device having a NAF cup having a vacuum port and an access port and also an attachment element for attaching a magnification means.

FIG. 2 shows a cup 10 for aspirating nipple fluid having a vacuum port 14 and an access port 16, and also having an attachment element 11 for attaching a loupe, lens or other glass or magnification means 13 to the cup for identifying activity at the nipple surface 19, e.g. for identifying the location from which any nipple aspirate is yielded under vacuum. The cup has a skirt 17 connected to the cup aperture 18. The access port 16 can have a seal 15 for maintaining the vacuum when the port is accessed with a tool. The attachment element can be a clip, snap, or other solid member capable of attaching to an attachable loupe, lens, or microscope. The loupe, lens or microscope should be positioned in sufficient proximity to the cup surface and/or the nipple surface to provide the practitioner visibility to identify activities at the nipple surface. The top surface or base 8 of the inverted cup is clear so that the practitioner can see through it when using the magnifying lens 3. To use the device of FIG. 2, the cup 10 is placed over the nipple so that the aperture of the cup 18 is approximately parallel to the nipple surface 19. Upon placement of the cup over the nipple, the skirt 17 is positioned on the skin and/or areola of the breast to create a seal. The cup aperture 18 will be positioned on or near the areola so that the nipple itself is centered in the chamber created by the inverted cup over the nipple. A syringe or other device capable of drawing air out of the chamber is attached (the syringe having been emptied of air) to the cup unit at the vacuum port 14. A loupe 13 or other magnification means is attached at the attachment element 11 for seeing the nipple surface through the top surface of the cup 12 in order to identify potential ductal orifices, identify fluid as it appears on the nipple surface both in order to collect the fluid, to identify a ductal orifice that fluid collects from, or in order generally to facilitate the NAF operation better by providing better visualization of the nipple surface. The access port 16 has a seal 15, e.g. a duck bill valve in the port, so that any tool that accesses the chamber and nipple surface through the port does not break the vacuum seal created by the syringe pulling back at the vacuum port.

Figure 3A:
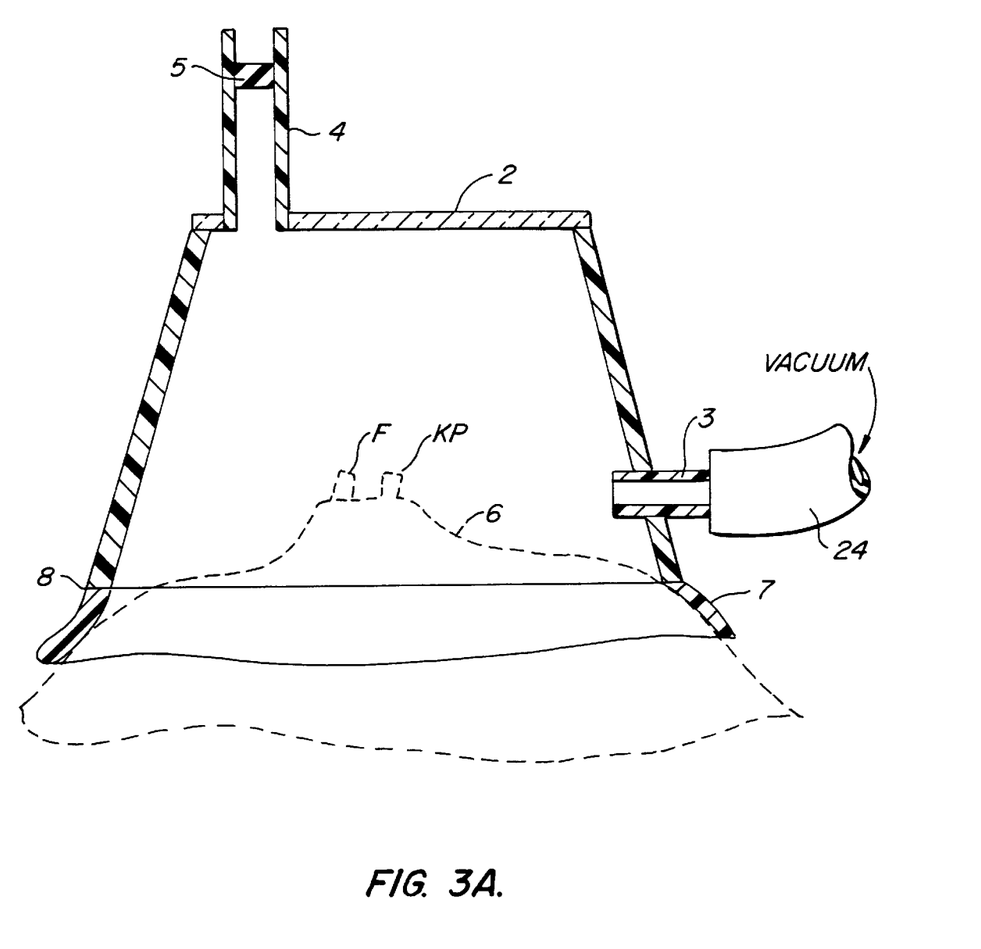
FIGS. 3A and 3B show use of the NAF cup with a collection tool capable of accessing the nipple surface.
Figure 3B:
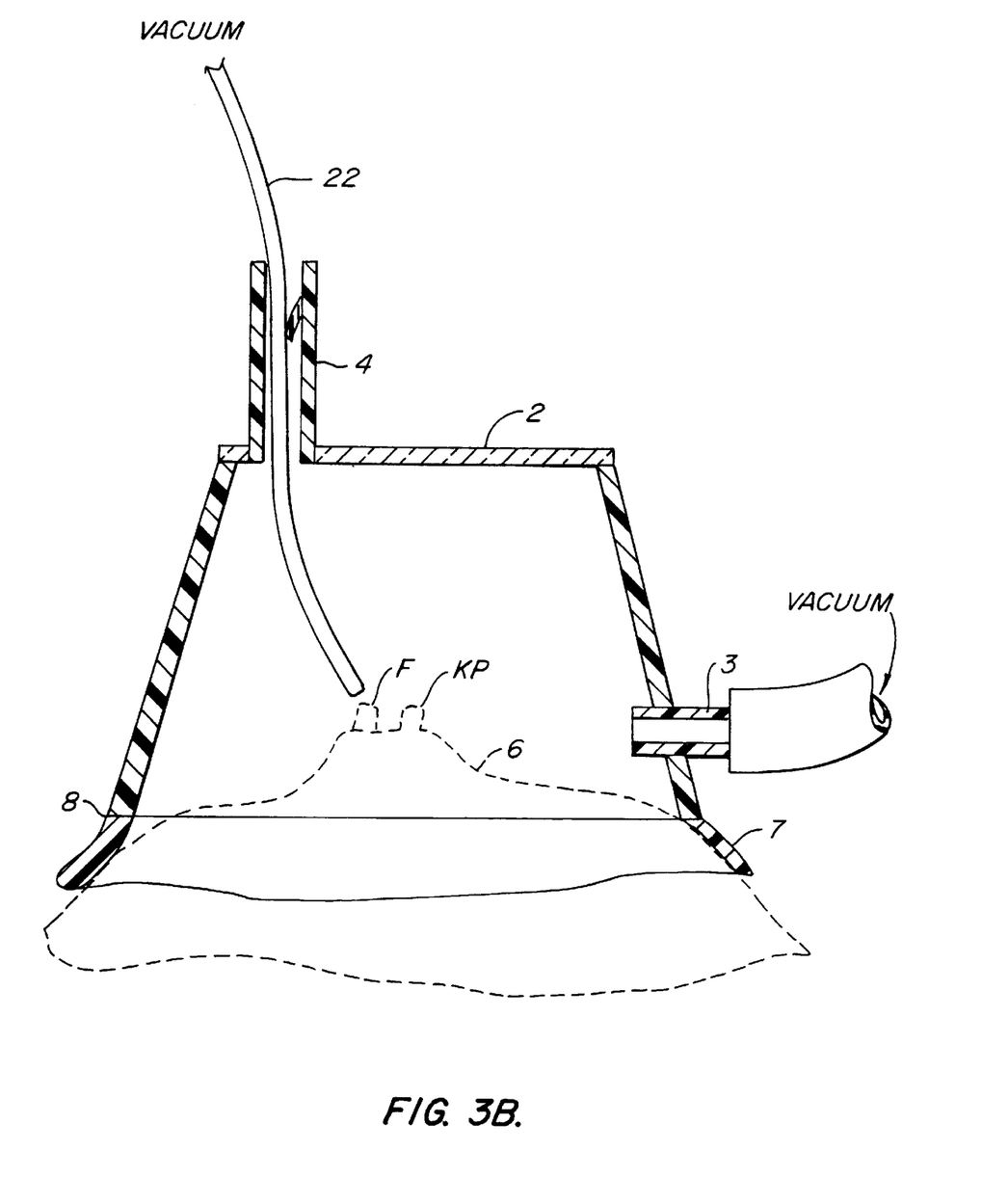

FIGS. 3A and 3B show the nipple aspiration cup 1 of FIG. 1, with collection tool 22 having a lumen and capable of accessing the nipple surface inserted through access port 4. The lumen of port 4 has a seal 5 to maintain the vacuum created through vacuum port 3. Vacuum is provided from an external source to draw fluid 20 from the nipple surface using the collection tool by applying suction in the lumen to draw off the fluid. The cup aperture 8 is placed over the nipple in such a way that the nipple is centered in the interior of the cup. The viewing window 2 of the cup 1 is approximately parallel to the surface of the nipple 6. An empty closed syringe or other vacuum generating tool 24 is placed at the vacuum port 3 and a vacuum drawn in the chamber. Access tool 22 (FIG. 3B) through the seal 5 in the lumen of the access port so that access to the nipple surface does not break the vacuum seal that has been created upon withdrawal of air from the chamber. The tip access tool 22 can contact the nipple surface 8 and collect fluid F or a keratin plus KP coming from a duct or ducts on the nipple surface.

Figure 4:
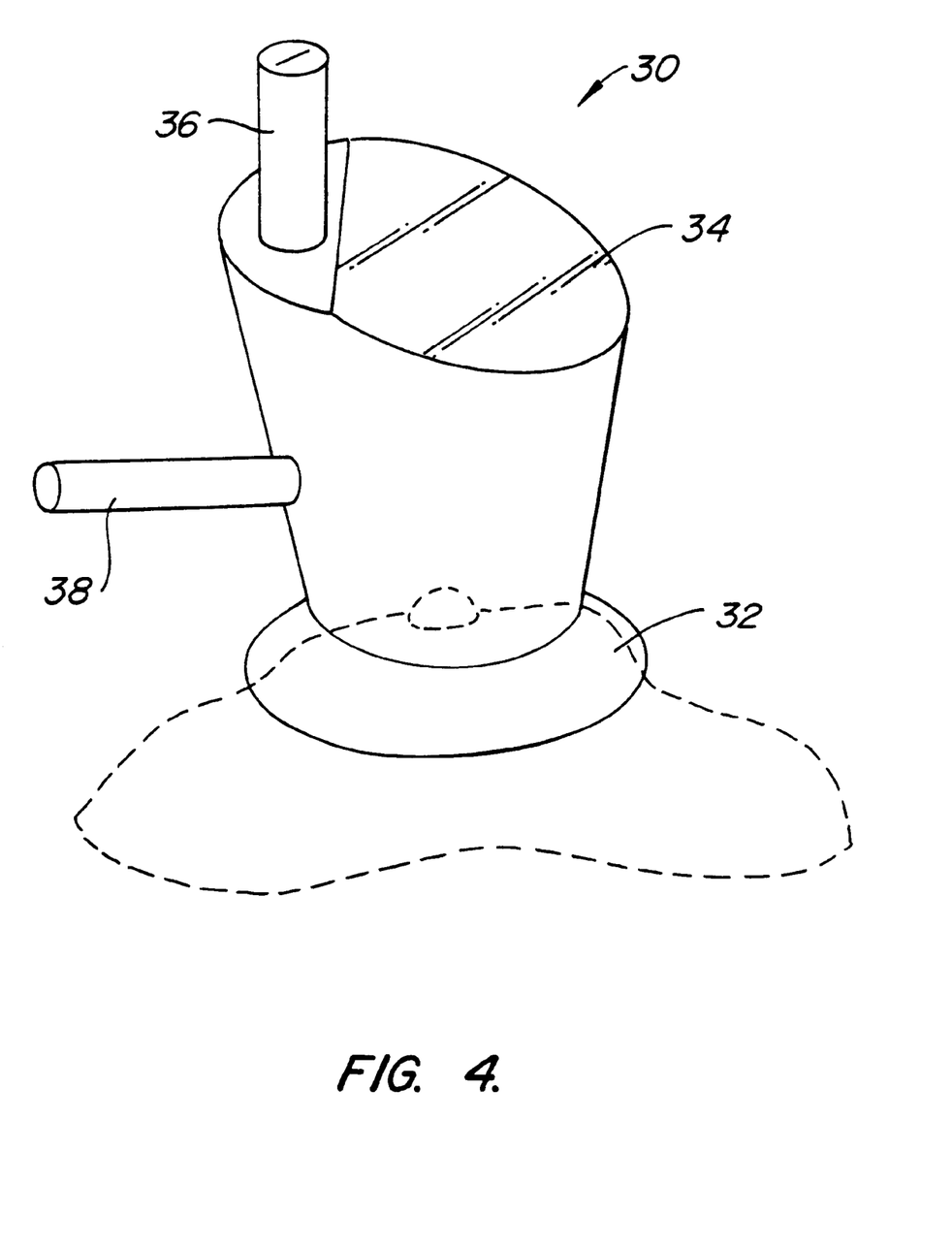
FIG. 4 shows a NAF cup having a conical shape, flexible skirt, and slanted elliptical base.

FIG. 4 shows an alternative nipple aspiration cup 30 having an inverted conical shape (laser at the top when placed over a nipple), a flexible skirt 32, having an elliptical window 34. An access port 36 is at the top of the cup next to window 34, and a vacuum port 38 is located on the sidewall of the cup 30. The conical shape of the cup provides a greater surface area for viewing and magnification, and the inclination provides a useful angle for visualizing the nipple surface as the tool as it is guided through any number of enumerated tasks. Use of the device depicted in FIG. 4 begins with placement of the cup 30 and its skirt 32 at the base of the nipple on or near the areola of that surrounds the nipple. An empty closed syringe or other tool (not shown) for pulling air from the chamber is placed at the vacuum port 38 for drawing a vacuum in the chamber. The window 34 is usually a magnifying lens in order to better observe the events on the nipple surface. Access port 36 may be accessed with a fluid retrieval tool to collect any fluid or other materials yielded in the vacuum chamber.

Use of the NAF device depicted in FIG. 5 provides the advantage of magnification on the sides of the cup, markings on the sides of the cup to indicate the rise of the nipple, and tape or strip-like attachments to hold the aperture at the breast after placement of the cup over the nipple. Breast 50 is contacted with a cup 52 having an aperture 54. Strips 56 are placed to fix the cup on the breast and facilitate a seal between the skin and the aperture. Cup 52 creates a volume or chamber around nipple 58. The cup sidewall is transparent, preferably with magnification, and has markings 60 to estimate a rise in the nipple under vacuum pressure. Top 62 of the cup 52 is smaller than bottom aperture 54 and contains vacuum port 64 for access by vacuum tool 66. Vacuum tool 66 is placed in the port 64, and a vacuum is draw by the tool to provide a gentle pull on the nipple and upward pressure on the nipple surface 4 from which fluid or other secreted materials can be seen through the transparent, optically magnified, sidewall.

Device 80 (FIG. 6A) can be used by placing the aperture 82 and skirt 84 over nipple 86 to create a seal. The skirt 84 has markings 88, and vacuum port 90 having threads 92 receives vacuum generating tool 94 having internal threads 96 compatible with threads 92, and the tool is screwed into the port. Vacuum is draw from the tool 94 and the chamber provides an environment that aspirates fluid from the nipple 86 that can be seen through magnified lens 97 positioned at an angle above the nipple. A top view of the device resting on the nipple (FIG. 6B) depicts nipple 86 circumscribed by lens 97 having port 90 off to the side, and below that resides aperture 82 surrounded by skirt 84.

The invention provides a kit comprising any of the devices described above for aspirating and retrieving breast duct fluid for analysis, and identifying a fluid-yielding ductal orifice, and further comprising instructions for use of the device. The instructions can detail the method of creating the vacuum pressure inside the enclosure, observing the nipple surface under magnification and identifying at least one ductal orifice, e.g. at a spot where fluid is secreted or a keratin plug is released. The magnification lens in or attached to the device can also be used to guide and control the process of accessing the nipple surface from the access port using an appropriate tool. Thus, the kit can further comprise a reagent or tool for marking the ductal orifice, a tool to access the duct, and/or a tool for collecting fluid from the duct. The tool for collecting fluid from the duct can comprise a lumen operably connected to a mechanism that provides suction in the lumen for drawing off fluid that collects on the nipple surface. The kit may also include reagents and items relating to preparation and preservation of the collected fluid for analysis. The kit also includes a container for holding the kit contents.

The ductal fluid is then examined to determine the presence of precancerous or cancerous ductal epithelial cells. The fluid sample (including ductal fluid that comprises ductal epithelial cells) can be analyzed by any effective means for identifying breast precancer or cancer. Thus the fluid itself can be analyzed for the presence of soluble factors or other components that might indicate the presence of cancerous or precancerous ductal epithelial cells in the duct. The ductal epithelial cells retrieved in the fluid can be analyzed for protein markers, nucleic acid markers, chromosomal abnormalities, or other characteristic changes that would signal the presence of cancerous or precancerous cells. In addition, other cells found in the fluid can also be analyzed, e.g. for an increase or decrease in these cells as compared to normal ductal fluid, or for qualities of these cells themselves. Thus, the fluid can be analyzed (e.g. for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers. In addition, the cells can be analyzed for morphological abnormalities in cell components, including, e.g. morphological abnormalities of the nucleus, cytoplasm, golgi apparatus or other parts of a cell. The cells can be analyzed for whether they do or do not aggregate (e.g. in clumps) or by making comparisons of the ductal epithelial cells with other cell types retrieved in the ductal fluid (e.g. macrophages, lymphocytes, foam cells and other possible components of ductal fluid). Ductal epithelial cells or components of the ductal fluid can be analyzed in situ, in the breast. In situ, in the breast, the ductal epithelial cells can be analyzed for their relationship to other (e.g. neighboring or distant) ductal epithelial cells, to other cells in the lumen or surrounding the lumen, (including e.g. myoepithelial cells), and for the molecular contents or the morphology of the ductal epithelial cells, including, e.g. protein markers, nucleic acid markers, biochemical markers in the cells or on the cell surfaces or for any evidence of neoplasia.

Some exemplary markers are listed below in the section that discusses monitoring patients. Many biological markers are listed in Porter-Jordan and Lippman, "Overview of the biological markers of breast cancer", Hematology/Oncology Clinics of North America vol. 8 (1):73–100, 1994). Some markers that are presently being studied by researchers presently include, carcinoma embryonic antigen (CEA), prostate specific antigen (PSA) Erb B2 antigen, gross cystic disease fluid protein-15 (GCDFP-15), and lactose dehydrogenase (LDH). For CEA see Imayama, Mori et al Cancer 1996, 78(6):1229–34; Inaji, Yayoi et al Cancer 1987,60(12):3008–13; Mori Int Conger Seer 1989, 807:211–8; Inaji, Koyama An To Kagaku Ryoho 1991, 18(2):313–7; Yayoi, Furukawa, et al Gan To Kagaku Ryoho 1994, 21 Suppl 2:133–9; Mori, Inaji, et al Jpn J Clin Oncol 1989,19(4):373–9; Foretova, Verselis, et al Proc Annu Meet Am Soc Clin Oncol 1995,14:A101; and Nishiguchi, Hishimoto et al Rinsho Byori 1992,40(1):67–72. For PSA see Foretova, Garber Lancet 1996,347(9015): 1631; Sauter E R. Daly M. Linahan K. Ehya H. Engstrom P F. Bonney G. Ross E A. Yu H. Diamandis E., Prostate-specific antigen levels in nipple aspirate fluid correlate with breast cancer risk, Cancer Epidemiology, Biomarkers & Prevention. 5(12):967–70, December; 1996 Sauter and Daly (1996) Proc Annu Meet Am Assoc Cancer Res 37:A1458; and Foretova and Garber (1996) Proc Annu Meet Am Assoc Cancer Res 37:A1446. For Erb B2 see Motomura (1995) Breast Cancer Res and Treat 33:89–92; and Inaji et al (1993) Tumor Biol 14: 271–8. For GCDFP-15 see Petrakis et al (1994) Proc Annu Meet Am Assoc Cancer Res 35:A1698. For LDH see Mannello et al (1995) Cancer 76:152–4; and Kawamoto (1994) Cancer 73:1836–41.

Chromosomal abnormalities in ductal epithelial cells can also provide information and act as a marker to identify cancer or precancer as described in Mark et al (1999) Cancer Genet Cytogenet 108:26–31; Lundlin and Mertens (1998) Breast Cancer Res Treat 51:1–15; Newsham (1998) Am J Pathol 153:5–9; Larson et al (1998) Am J Pathol 152:1591–8; Adelaide et al (1998) Genes Chromosomes Cancer 22:186–99; Fejzo et al (1998) Gene Chromosome Cancer 22:105–113; Dietrich et al (1998) Hum Pathol 12: 1379–82; Cavalli et al (1997) Hereditas 126:261–8; Adeyinka et al (1997) Cancer Genet Cytogenet 97:119–21; Afify and Mark (1997) Cancer Genet Cytogenet 97:101–5; Brenner and Aldaz (1997) Prog Clin Biol Res 396: 63–82; Mark et al (1997) Ann Clin Lab Sci 27:47–56; and Fabian et al 1993 J. Cellular Biochemistry 17G: 153–16.

In addition, exemplary markers are described in Masood S., (Prediction of recurrence for advanced breast cancer. Traditional and contemporary pathologic and molecular markers) Surgical Oncology Clinics of North America. 4(4):601–32, 1995; Lopez-Guerrero et al (1999) J Hematother 8(1):53–61; Marjumdar and Diamandis (1999) Br J Cancer 79(9–10):1594–602; Balleine et al (1999) Br J Cancer 79 (9–10):1564–71; Houston et al (1999) Br J Cancer 79(7–8):1220–6; Nikolic-Vukosavljevic et al (1998) Tumori 84(6):691–4; Maguire et al (1998) Int J Biol Markers 13(3):139–44; Steams et al (1998) Breast Cancer Res Treat 52(1–3):239–59; Eiriksdottir et al (1998) Eur J Cancer 34(13):2076–81, and U.S. Pat. No. 5,169,774. Many known breast cancer markers are discussed and described in readily available medical text books on breast cancer. In addition, several markers can be identified and analyzed in the same sample, e.g. Fabian et al 1993 J. Cellular Biochemistry 17G:153–16 and Fabian et al 1994 Breast Cancer Res Treat 30(3):263–74 looking at estrogen receptor (ER), epidermal growth factor receptor (EGFR), mutant p53, HER-2 neu by immunohistochemistry and aneuploidy by image analysis in fine needle aspirates.

Examination of the ductal epithelial cells can be accomplished by examining useful indicators such as, e.g. the morphology of the cells or cellular contents. The cellular contents can include, e.g. protein, nucleic acid, or other molecular markers in the cells. Cell morphology can serve to establish whether the ductal epithelial cells are normal (i.e. not precancerous or cancerous or having another non-cancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma). Analysis of cell contents may serve to establish similar staging as established by morphology, capturing generally a progression of a precancerous or cancerous condition in the cells.

Cytological assays that can be performed on the cells retrieved from a duct or from nipple aspirate can include e.g. assays described in King et al, J. Nat'l Cancer Inst (1983) 71:1115–21, Wrensch et al. (1992) Am. J. Epidem. 135: 130–141, Papanicolaou et al, (1958) Cancer, 11:377–409 and Goodson W H & King E B, Chapter 4: Discharges and Secretions of the Nipple, THE BREAST: COMPREHENSIVE MANAGEMENT OF BENIGN AND MALIGNANT-DISEASES (1998) 2nd Ed. vol 2, Bland & Kirby eds. W. B. Saunders Co, Philadelphia, Pa. pp. 51–74. For example, as described in Goodson and King (page 60) atypical hyperplasia presents having cellular abnormalities, increased coarseness of the chromatin and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) J. Natl Cancer Inst 59: 1073–1080 and King et al, (1983) JNCI 71(6) 1115–1121. Atypia and carcinoma in situ are widely characterized pathologically, as described in Page et al, (1998) Mod Pathol 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, American Society of Clinical Pathology: November 199S, "Cytopathology of the Breast" ISBN 0891893806; and Feldman P S, American Society of Clinical Pathology, November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, "Can FNA biopsy separate atypical hyperplasia, carcinoma in situ, and invasive carcinoma of the breast?: Cytomorphologic criteria and limitations in diagnosis, Diagnostic Cytopathology. 9(6):713–28, 1993; Masood et al, (Immunohistochemical differentiation of atypical hyperplasia vs. carcinoma in situ of the breast.) Cancer Detection & Prevention. 16(4):225–35, 1992; Masood et al, (Cytologic differentiation between proliferative and nonproliferative breast disease in mammographically guided fine-needle aspirates) Diagnostic Cytopathology.7(6):581–90, 1991; Masood S. (Occult breast lesions and aspiration biopsy: a new challenge) Diagnostic Cytopathology. 9(6):613–4, 1993; Masood S., (Prognostic factors in breast cancer: use of cytologic preparations) Diagnostic Cytopathology. 13(5):388–95, 1995; Novak and Masood, (Nuclear grooves in fine-needle aspiration biopsies of breast lesions: do they have any significance?) Diagnostic Cytopathology. 18(5):333–7, 1998; Sidawy et al, "Interobserver variability in the classification ofproliferative breast lesions by fine-needle aspiration: results of the Papanicolaou Society of Cytopathology Study" Diagnostic Cytopathology. 18(2):150–65, 1998; Masood et al, "Automation in cytology: a survey conducted by the New Technology Task Force, Papanicolaou Society of Cytopathology" Diagnostic Cytopathology. 18(1):47–55, 1998; and Frykberg and Masood Copeland E M 3d. Bland K I., "Ductal carcinoma in situ of the breast" Surgery, Gynecology & Obstetrics 177(4):425–40, 1993.

In addition to some markers discussed and/or articles or books cited on breast cancer and breast precancer markers, the following cancer markers are listed here as exemplary and may be used as well as other markers to analyze the condition of a breast duct. Standard assay procedures for identifying the markers can be used, including antibodies or other binding partners, labels, stains, pattern analysis (for cells and cell components), and in general any other chemical or visual identification techniques. The following are exemplary potential markers for such identification and analysis:

cathepsins (including cathepsin D)

maspin, fas, fas ligand, tissue inhibitor of matrix metalloproteinas-1 (TIMP-1)

chemokines (both C—C and C—X—C type chemokines)

collagenases, metalloproteinases, TIMP's, cathepsins, disrupted basement membrane epitopes, stromolysin-3 cytokeratins (e.g. keratin 14, B1, KA1, KA4 and 312C8-1)

estrogen and progesterone receptors (or any androgen or other steroid receptor)

growth factor receptors for members of the fibroblast growth family (FGF) including FGF1-18, vascular endothelial growth factor (VEGF), insulin-like growth factor-1 (IGF-I), IGF-II, platelet-derived growth factor (PDGF), keratinocyte growth factor (KGF), and epithelial growth factor (EGF), placental growth factor (PLGF), hepatocyte growth factor (HGF), tumor necrosis factor (TNF), transforming growth factor (TGF) both alpha and beta forms, and angiopoietin, for example growth factors and cytokines including FGF1-18, VEGF, IGF-I, IGF-II, PDGF, KGF, EGF, PLGF, HGF, TNF, TGF alpha and beta, angiopoietin, for example heat shock proteins (HSP) (e.g. HSP27) 27 (HSP27)

ErB type 1 tyrosine kinase receptors (e.g. Her2 (an EGF receptor) or any ligand or receptor of the ErbB family of ligands and receptors)

integrins, selectins, cadherins, for example (i.e. alpha and beta 3 integrin)

keratin-14 known cancer antigens including, for example Ki-67, Ki-S1, p53, nm23, bcl-2, p21 ras, cyclins, and pS2

Thrombin receptor activating peptide urokinase, urokinase-type plasminogen activator (UPA), plasmin antiplasmin, UPA receptor (UPAR), fibrinogen, plasmin activator inhibitor-1 and 2 (PAI-1 and 2)

telomerase antibodies to tumor associated antigen-72 (TAG-72) (e.g. B72.3, B6.2, and TKH2)

carcinoembryonic antigen (CEA) (see e.g. EP 319,686)

prostate specific antigen (PSA)

gross cystic disease fluid protein-15 (GCDFP-15)

lactose dehydrogenase (LDH)

chromosomal abnormalities (e.g. aneuploidy or other abnormalities)

S1 protein alkaline phosphatase myosin sialyl Tn (STn) glycopeptide (e.g. TAG-72)

Tn glycopeptide

EXAMPLES

1. Nipple Aspiration of Right and Left Breast of Pre-Menopausal Woman: Identification and Marking of Yielding Ducts and Duct-Specific Fluid Collection.

A female patient classified as high risk for breast cancer due to family history consents to a procedure that will include nipple aspiration, and marking of the yielding breast ducts. Fluid from yielding ducts will be collected, either pooled in the NAF cup or separately if possible. The patient's nipples are cleaned with antiseptic and dekeratinized with ceruminex. An inverted cone NAF device having a magnified base larger than the aperture of the cone and also having a flexible skirt extending about 2 centimeters and surrounding the aperture is applied to the right nipple and breast. A syringe draws air from the enclosure at a port on the side of the cup. A tool comprising the ability to mark and/or collect fluid from the nipple surface is placed in the access port at the top of the cup in readiness for marking or collecting.

The practitioner observes the nipple under vacuum through the magnification lens at the base of the cup for the first hint of fluid yielding from a duct. Upon such occurrence, the practitioner, while still holding the cup tightly on the patient's breast, moves a capillary tube lumen coated at the tip circumference of the lumen with a semipermanent dye or ink that stains the skin region at the ductal orifice on contact. The capillary lumen contacts the fluid and the fluid is drawn into the lumen by a capillary action. The fluid is analyzed by cytological techniques on a slide with a standard cytological stain using a light microscope. The cells are studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, American Society of Clinical Pathology: November 199S, "Cytopathology of the Breast" ISBN 0891893806; and Feldman P S, American Society of Clinical Pathology, November 1984, "Fine Needle Aspiration Cytology and Its Clinical Applications: Breast and Lung" ISBN 0891891846.

A second duct yielding fluid on the right nipple is likewise marked with ink at the end of the capillary tube and the fluid collected into the capillary tube. The fluid collected in the capillary tube is released onto a filter or slide for analysis. The cells in the fluid are analyzed by cytology.

Depending on the results of the cytological analysis, the marked ducts are later accessed or studied to follow any developments of a condition including atypical ductal hyperplasia or carcinoma in the breast. The process is repeated on the left breast. Cytologically analyzed samples are saved and if the patient indicates atypical hyperplasia or suspect abnormalities in any of the ducts, the duct is monitored regularly.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for aspirating and retrieving breast duct fluid comprising:

an enclosure adapted to be seal against the base of a human breast nipple, said enclosure comprising an interior volume, an aperture adapted to circumscribe the human breast nipple, a vacuum port for connection to a vacuum source for creating a vacuum in said interior volume, and a magnifying lens forming a portion of the enclosure, wherein the magnifying lens is positioned to permit a practitioner to observe the nipple within the aperture.

2. A device as in claim 1, wherein the enclosure has at least one access port for providing access to a nipple surface with a tool and the device further comprises a pneumatic seal within the at least one access port to maintain a vacuum before and during access with the tool.

3. A device as in claim 2, wherein the at least one access port is adapted to receive a tool selected from the group consisting of a ductal orifice marking tool and a ductal fluid retrieval tool.

4. A device for aspirating and retrieving breast duct fluid comprising:

an enclosure adapted to be seal against the base of a human breast nipple, said enclosure comprising an interior volume, an aperture adapted to circumscribe the human breast nipple, and a vacuum port for connection to a vacuum source for creating a vacuum in said interior volume;

a window in the enclosure that provides visual access to a nipple surface; and an anchor structure on the exterior of the device to which a magnifying tool can be removably attached so that a practitioner can see a magnified nipple through a surface of the window under a vacuum.

5. A device as in claim 4, wherein the enclosure has at least one access port for providing access to the nipple surface with a tool and the device further comprises a pneumatic seal within the at least one access port to maintain a vacuum before and during access with the tool.

6. A device as in claim 5, wherein the at least one access port is adapted to receive a tool selected from the group consisting of a ductal orifice marking tool and a ductal fluid retrieval tool.

7. A device as in claim 1 or 4, further comprising skirt of a flexible material connected to the aperture, wherein the flexible material is capable of maintaining a seal with the breast skin.

8. A device as in claim 1, wherein the magnifying lens is positioned at an angle relative to a plane of the aperture.

9. A device as in claim 1, wherein the device further comprises threads disposed adjacent the vacuum port for screwing a compatibly threaded vacuum source into the port.

10. A device as in any of claims 1–6 and 8–9, further comprising a package holding the device wherein the device is sterilized and maintained in the package.

11. A method of identifying a breast milk duct having a ductal orifice wherein the duct is capable of yielding fluid or releasing a keratin plug upon aspiration in a vacuum, said method comprising:
  (a) placing a device for aspirating and retrieving breast duct fluid on a breast of a patient so that a nipple is received within said device, said device comprising an enclosure for sealing against a base of the nipple, said enclosure comprising an aperture adapted to circumscribe the nipple, a vacuum port for connecting to a vacuum source and a magnification tool,
  (b) applying a vacuum to the device through the vacuum port, and
  (c) viewing a surface of the nipple through said magnification tool while the device remains in place to identify at least one ductal orifice from which fluid is secreted or a keratin plug is released under the vacuum.

12. A method as in claim 11, further comprising performing a task selected from the group consisting of marking, accessing and collecting fluid from the duct by placing a tool through an access port and contacting the nipple surface to perform the task while the device remains in place on the nipple.

13. The method of claim 12, wherein marking comprises marking the ductal orifice with a reagent or tool selected from the group consisting of dye, ink, pen, plug, and wire.

14. The method of claim 12, wherein accessing the duct comprises accessing the duct with a tool selected from the group consisting of a tool comprising a lumen, a tool comprising a shaft without a lumen, and a fiberoptic endoscope.

15. The method of claim 12, wherein collecting fluid from the duct comprises collecting fluid with a tool comprising a lumen or an absorbent material.

16. The method of claim 11, wherein the device was sterilized prior to placing the device on the nipple.

17. A method of identifying a breast milk duct having a ductal orifice wherein the duct is capable of yielding fluid or releasing a keratin plug upon aspiration in a vacuum, said method comprising:
  (a) placing a device for aspirating and retrieving breast duct fluid on a breast of a patient so that a nipple is received in said device, said device comprising an enclosure for sealing against a base of the nipple, said enclosure comprising an aperture adapted to circumscribe the nipple, a vacuum port for connecting to a vacuum source, and at least one access port for providing access to a surface of the nipple with a tool, the at least one access port including a pneumatic seal for maintaining a vacuum before and during access with the tool;
  (b) applying a vacuum to the device through the vacuum port, and
  (c) viewing the nipple through a magnification tool while the device remains in place to identify at least one ductal orifice from which fluid is secreted or a keratin plug is released under the vacuum.

18. A device as in claim 4, wherein the magnifying tool comprises a loupe, a lens or a microscope.

* * * * *